United States Patent [19]

Wallace et al.

[11] Patent Number: 4,515,021

[45] Date of Patent: May 7, 1985

[54] INTERVALOMETER TIME MEASUREMENT APPARATUS AND METHOD

[75] Inventors: David R. Wallace, Milton; James M. Korba, Woburn; James E. Matson, Brookline; Lawrence C. Lynnworth, Waltham, all of Mass.

[73] Assignee: Panametrics, Inc., Waltham, Mass.

[21] Appl. No.: 518,738

[22] Filed: Jul. 29, 1983

[51] Int. Cl.³ .................................................. G01F 1/66
[52] U.S. Cl. ..................................... 73/861.27; 73/597
[58] Field of Search ...................... 73/861.27–861.31, 73/597, 900, 631; 367/27, 28, 127; 307/354

[56] References Cited

U.S. PATENT DOCUMENTS

| | | |
|---|---|---|
| 3,869,915 | 3/1975 | Baumoel . |
| 3,918,304 | 11/1975 | Abruzzo et al. ................. 73/861.29 |
| 3,954,008 | 5/1976 | Yamamoto et al. . |
| 3,981,191 | 9/1976 | Brown et al. . |
| 4,022,058 | 5/1977 | Brown . |
| 4,028,938 | 6/1977 | Eck ..................................... 73/861.31 |
| 4,080,574 | 3/1978 | Loosemore et al. ............. 73/597 X |
| 4,172,250 | 10/1979 | Guignard ............................... 367/27 |
| 4,183,244 | 1/1980 | Kohno et al. .................... 73/861.28 |
| 4,205,555 | 6/1980 | Hashiguchi ....................... 73/631 X |
| 4,232,548 | 11/1980 | Baumoel . |
| 4,451,797 | 5/1984 | Bains, Jr. ......................... 73/631 X |

OTHER PUBLICATIONS

Mitsuta, "Sonic Anemometer–Thermometer for Atmospheric Turbulence Measurements", in *Flow, its Measure and Control in Science and Industry*, Dowdell (Ed.), vol. I, Part I, pp. 341–344, Instrument Society of America, 1974.

Schmidt, "Acoustical Method for Fast Detection and Measurement of Vortices in Wind Tunnels", ICIASF '75 Record, pp. 216–218, 1975.

Crawford et al., "Multipath Artifact Corrections in Ultrasonic Transmission Tomography", *Ultrasonic Imaging*, vol. 4, pp. 234–266, 1982.

"Linear Databook", National Semiconductor Corporation, pp. 9-79—9-84, 1982.

Biber et al., "The Polaroid Ultrasonic Ranging System", Audio Engineering Society, pp. 6–7, 1980.

*Primary Examiner*—Charles A. Ruehl
*Attorney, Agent, or Firm*—Lahive & Cockfield

[57] ABSTRACT

An intervalometer for determining the transit time of an ultrasonic energy pulse through a fluid medium employs an automatic gain control amplifier circuit for amplitude stabilizing the electrical signal derived at a receiving transducer. The automatic gain control circuit tracks both a rapidly increasing and a rapidly decreasing signal amplitude. In various embodiments, synchronous switching can be employed in conjunction with a single amplifier and a plurality of storage elements to rapidly scan a plurality of signal paths and for providing automatic gain control capability on each path. The intervalometer further has a "slipped cycle" capability for accurately determining arrival time when is is known that the signal pulse will be within a certain range of times. In addition, the relative time difference between two arriving signal pulses can be accurately determined using this method so long as the range of time difference is sufficiently small. The intervalometer also provides for bad data rejection based upon limits applied to either transit time or signal amplitude.

28 Claims, 12 Drawing Figures

INTERVALOMETER TIME MEASUREMENT APPARATUS AND METHOD

The invention relates in general to an apparatus and method for measuring time intervals and in particular to a time measurement apparatus and method for accurately determining the time of arrival of a bandwidth limited pulse of ultrasonic energy.

CROSS REFERENCE TO RELATED APPLICATIONS

This application is related to Lynnworth and Matson, U.S. application Ser. No. 518,344, filed July 29, 1983, and entitled "Integrated Threshold Arming Method and Apparatus" and to Smalling et al, U.S. application Ser. No. 518,444, filed July 29, 1983, and entitled "Apparatus and Methods for Measuring Fluid Flow Parameters." To the extent they are not already described in this application, U.S. Ser. Nos. 518,344, and 578,444, are incorporated herein by reference.

BACKGROUND OF THE INVENTION

There exist many fields wherein accurate measurement of a time duration is critical to the success of a system analysis. In many instances, the time interval of measurement is determined by transmitting a relatively short pulse of energy (having a wide bandwidth) and precisely measuring the arrival time of the received return pulse. Typically, however, the return pulse is not identical to the transmitted pulse and in many instances the return pulse can be severely affected by the media through which the pulse travels. Typical examples of the use of a measured time interval are the radar and sonar environments wherein the time interval measures distance from the source to an object, for example, an airplane or the sea bottom. Another example of the use of time interval measurement is flow detection and measurement using ultrasonic signal energy, such as that described in Lynnworth, U.S. Pat. No. 3,575,050, issued April 13, 1971, wherein a short pulse of ultrasonic energy is transmitted through a moving fluid in an upstream and a downstream direction. The time intervals of upstream and downstream travel provide measurement data useful in determining fluid flow.

In many instances, the detection of the arrival time of an ultrasonic pulse passing through a fluid is affected significantly by factors such as turbulent flow conditions, high flow velocities, and changes in fluid temperature, pressure, and composition. Thus, an ultrasonic energy pulse propagating through a fluid can be subject to different and rapidly varying amounts of attenuation. However, in an ultrasonic measuring system, wherein it is the arrival time of the ultrasonic pulse which is relevant to the fluid property being measured, the detection process is often a difficult one due to amplitude variations of the received pulse. Typically, according to earlier apparatus, automatic gain control (AGC) circuitry has been employed for electronically reducing the amplitude fluctuations to improve both the reliability and the accuracy of the detection process.

Due to the pulsed nature of the received signals, wherein there are relatively long periods wherein no signal is present, a gated fast attack, slow decay type of automatic gain control, directed to "tracking" the signal envelope, has been traditionally employed. This type of automatic gain control can rapidly and accurately track an increasing signal due to its fast attack time; however, because the decay time is usually much slower than the rate at which the ultrasonic pulses are received, rapidly decreasing signals cannot be tracked.

Further, in many instances, the interval measuring apparatus will be employed in connection with measuring the arrival time along several different transmission paths. The amplitudes of the signals on the various paths will often differ considerably due to the differences in transducers employed, path geometry, and flow variables. It is also important in many instances to interrogate the paths quite rapidly. The variation in the received signal amplitude along the different paths, along different zones in a given path, or in opposite directions over a given path, however, can result in detection errors if the automatic gain control signal does not "follow" the separate paths accurately. Traditionally, therefore, when multiple paths have been employed, either a separate automatic gain control receiver has been employed in connection with each path or a single automatic gain control receiver has been employed with an interrogation rate on each path which is sufficiently slow to allow the automatic gain control amplifier sufficient time to correct for the different received amplitudes along the respective paths. The first method clearly requires a plurality of receivers which is costly and the second method is limited to a very slow interrogation rate, typically less than the desired pulse repetition rate.

In addition to the use of automatic gain control, in the ultrasonic flow measurement application in particular, the received pulse typically appears as though it were transmitted through a narrow band filter. Thus, in time, the extent of the pulse increases; and therefore, when accurate time durations are required, it is often difficult to exactly measure, consistently, when the pulse is received. In those instances where the time of receipt remains substantially constant from pulse transmittal to pulse transmittal, relatively standard procedures are available for accurately determining the time when the pulse is received. Thus, for example, a typical approach is to measure the amplitude of the returning pulse; and, when that amplitude exceeds a fixed voltage threshold value, to set the time of receipt as the time of the next zero crossing of the pulse signal. This method is adequate in relatively noise free environments, or where the transit time is relatively constant from measurement to measurement, and, under those circumstances, produces an accurate "relative" time duration. In the ultrasonic flow measurement system, it is the difference in transit time of the upstream and downstream pulse signals which is most important and hence the arrival time, if determined in a consistent manner (even if the time measurement contains a constant error), is usually adequate for measuring the flow within the pipe.

In many flowmeters, however, there is significant noise on the received signal from, for example, interference within the pipe due to either turbulence or pipeline irregularities. In other instances, the transit time varies significantly due to time varying flows and turbulence of the flow. As a result, a typical zero crossing measurement based upon the amplitude threshold method described above, proves inadequate to the task of determining, with a high degree of accuracy, the pulse receive time for a narrow bandwidth pulse signal. In essence, the difficulty is determining the same zero crossing, for example the fifth, for each and every pulse signal received.

It is therefore an object of this invention to accurately measure the time of arrival of a narrow bandwidth pulse signal. Another object of the invention is accurately determining the arrival time of an ultrasonic pulse signal in a volumetric flow measuring environment. Further objects of the invention are a reliable, accurate, easily maintained intervalometer apparatus and method for accurately determining the arrival time of a pulse signal under conditions of varying flow rates and turbulence of the flow. Yet further objects of the invention are an intervalometer method and apparatus which is cost effective to build and easy to manufacture.

SUMMARY OF THE INVENTION

The invention relates to an intervalometer for determining the transit time of ultrasonic energy traversing a fluid medium. The intervalometer features a transmitting transducer for emitting a pulse of ultrasonic energy, a receiving transducer for receiving the ultrasonic energy and for generating an electrical signal in response thereto, an automatic gain controlled amplifier for amplitude stabilizing the electrical signal, the amplifier having circuitry for tracking both rapidly increasing and rapidly decreasing signal amplitude, and a transit time measurement circuit responsive to the stabilized electrical signal for determining the transit time.

More particularly, the gain controlled amplifier circuit features a gated, resettable amplitude detector connected to receive the stabilized signal, a storage element switchably connected to the amplitude detector for storing a signal representative of the stabilized signal amplitude, a differential integrator having a control signal output and being switchably connected to the storage element and a signal reference level. The invention, in this aspect, further features a controlled gain amplifier connected to and controlled by the control signal output of the integrator, elements for connecting the detector to the storage element during receipt of an energy signal and for connecting the integrator to the storage element during a time duration following receipt of the energy signal, the storage element being connected to one and only one of the detector and integrator at one time. Circuitry is also provided for resetting the integrator prior to receipt of a next energy pulse.

In another aspect, the intervalometer of the present invention relates to determining the transit time of ultrasonic energy traversing the fluid medium along a plurality of paths. In this aspect, the intervalometer features an automatic gain controlled amplifier circuit for providing an amplitude stabilized output signal in response to an electrical signal input thereto, the "stabilization" provided to the output signal being set according to a control signal input. There are further featured a plurality of controlling storage elements, each storage element, when connected to the gain controlled amplifier, providing the control signal input thereto. Synchronous switching members having a first and second switch wherein each switch connects a selected one of a plurality of switch input lines to a switch output line and the switches connect a selected one of the receiving transducer output signals to the gain controlled amplifier and synchronously connects a selected one of the controlling storage elements to the gain controlled amplifier. Thereby, a single gain controlled amplifier can be rapidly cycled among the receiving transducers.

In yet another aspect of the invention, an intervalometer measuring method features the steps of transmitting an ultrasonic energy pulse and receiving the pulse, measuring the transit time of the energy pulse based upon an event recognition in the received electrical signal. The invention further features an energy pulse having a plurality of repeating cycles, the event recognition being based upon a characteristic of one of the cycles, such as the zero crossing of a particular cycle, and the cycles being characterized by a repetition period. The method further features adjusting the measured transit time of the energy pulse by changing the transit time by one or more periods of the received energy pulse so that the difference between the adjusted transit time and an expected value is within a predetermined range.

In another aspect of this "slipped cycle" method of operation, the invention features a measurement method having the steps of measuring an upstream and a downstream transit time based, in each case, upon an event recognition in the received energy pulse. The invention further features an energy pulse having a plurality of repeating cycles, the event being characteristic of one of the cycles, and the cycles being characterized by a repetition period. The method further features generating a measurement of the time difference by differencing the upstream and downstream transit times and adjusting the transit time difference by multiples of the repetition period until the difference is within a predetermined time range.

In yet another aspect of the invention the intervalometer has circuitry for determining amplitude limits of the stabilized electrical signal output from an automatic gain control circuit, and for providing a bad signal indication when the amplitude of the stabilized signal is outside a predetermined allowable range of values or when the stabilized signal differs from a reference signal (such as a previously "good" signal) by a designated amount such as 1, 2, or 3 dB. The method further features a transit time measurement element responsive to the stabilized electrical signal for determining the transit time and being responsive also to the bad signal indication for determining whether the transit time represents bad data.

In a particularly perferred embodiment wherein narrowband signals are being received, the invention features measuring circuitry which advantageously employs an integrated threshold arming circuit operating together with one or more of the automatic gain control circuits, the amplitude discrimination means, the slipped cycle means, and a bad data analysis means.

DESCRIPTION OF THE DRAWINGS

Other objects, features, and advantages of the invention will be apparent to those practiced in the art from the following description taken together with the drawings in which.

DESCRIPTION OF A PREFERRED EMBODIMENT

Figure 1:
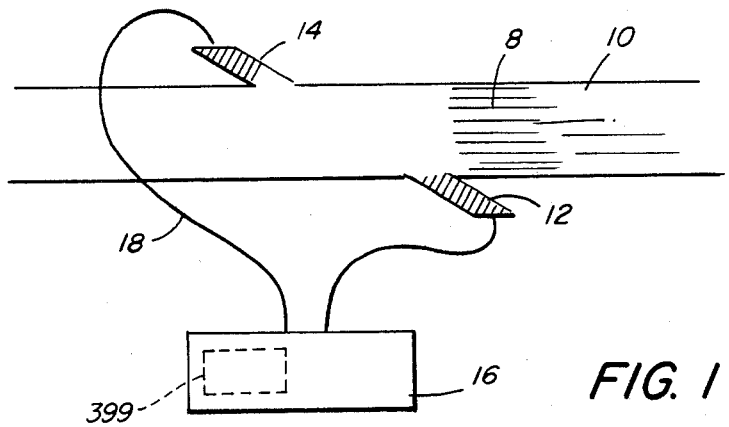
FIG. 1 is a schematic block representation describing a typical application of the inventive apparatus and method.

Referring to FIG. 1, the invention is particularly useful in connection with measuring the volumetric flow of a fluid 8 through a conduit or pipe 10. The fluid can be either a gas or a liquid, can flow in either direction, can have a rapidly varying flow rate, and can be characterized as a laminar flow, a transitional flow, or a turbulent flow. The varying flow rate, flow profile, and fluid composition and state conditions will generally affect the time interval between the transmission and reception of a pulse of energy from one transducer, for example a transducer 12, and a second transducer, for example transducer 14. The method and apparatus for using ultrasonic pulses for determining fluid flow is well described in, for example, U.S. Pat. No. 3,575,050 referred to above.

Intervalometer 16 of the present invention is designed to measure, precisely and reliably, the time interval between the transmission of a pulse and its receipt. Typically, the transmitted pulse is a wide band, time limited pulse, such as that illustrated in line (a) of FIG. 2. However, even if the transmitted pulse is a relatively wide band and hence "sharp" pulse, the received pulse often has the appearance of the pulse shown in line (b) of FIG. 2. This pulse has a relatively slowly increasing amplitude, that is, the difference in amplitude from "peak" to "peak" is relatively small. For the pulse shown in FIG. 2, a pulse having a "Q" of about ten, the difference in amplitude from amplitude peak to amplitude peak of the first few cycles may be only ten percent. Consequently, small amounts of noise or other interference can easily upset an amplitude threshold arming procedure, after which arming, the first zero crossing determines the time of arrival of the pulse signal. The shape of the pulse in line (b) of FIG. 2 can occur due to resonant effects of the structure of, for example, the pipe walls, the layered media through which the pulse is traveling, or natural resonances in the transducers used for the ultrasonic pulse transmission and reception. Material characteristic resonances can also affect the received signal pulse shape.

In practice, when measuring relatively uniform homogeneous materials, the value of the received amplitude will not vary significantly from moment to moment. Under these circumstances, the conventional and widely used amplitude threshold method of "arming," followed by a zero crossing detection generally provides quite satisfactory results. On the other hand however, in connection with inhomogeneous solids such as concrete, fiberglass, reinforced plastic, wood, biological specimens, etc., in which the attenuation varies spatially, scanning the media ultrasonically provides a received amplitude which varies temporally, that is, from time moment to time moment, depending upon the region interrogated. Similarly, if an inhomogeneous or turbulent fluid is interrogated ultrasonically, the received amplitude will again vary temporally and, depending upon the nature of the flow, rather unpredictably. In some instances, even changing the direction of interrogation changes the shape and amplitude of the received pulse. (The amplitude change is discussed by Ingard and Singhal in J. Acoustical Society of America, Vol. 60, pp. 1213–1215 (1976), and is based upon laboratory tests in small conduits.) In relatively large conduits typical of a flare stack system in petrochemical refineries, for example especially for high flow rates, the amplitude and phase jitter is quite pronounced and can contain components well above 1 Hz. In such cases, even automatic gain control (AGC) circuits, which are typically used for optimizing the response of the system, cannot prevent some degree of fluctuation in the received amplitude. They can also not prevent a change of pulse shape if conditions vary substantially from one cycle to another.

Accordingly therefore, the usual arming methods which are based solely on the amplitude of the received signal are not sufficiently reliable for the narrow band signal. As noted above, the change of amplitude from one cycle to the next, for a signal having a "Q" of about ten, is not in excess of about ten percent or one dB. Therefore, if jitter in the received signal exceeds one dB, the zero crossing detector will often be falsely armed at the wrong cycle if the conventional amplitude based arming method is used.

According to the invention therefore a different method and apparatus are employed. The basic arming method and apparatus herein disclosed are applicable independent of the number of transducers, and in particular, are applicable for the "pulse-echo" mode of operation where the same transducer functions as both a transmitter and a receiver.

Figure 3:
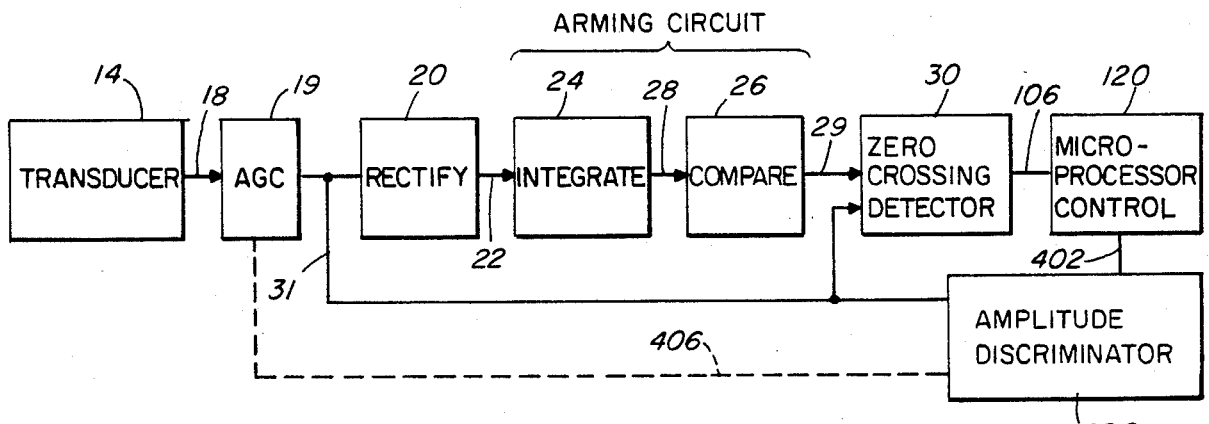
FIG. 3 is an electrical block schematic showing the major components according to the invention.

Referring to FIG. 3, in the illustrated embodiment of the invention, the transducer 14 provides a received output signal over a line 18. The received signal, in the illustrated embodiment, is processed through an automatic gain control circuit 19 and is half wave rectified by a rectification circuit 20. The rectified output over a line 22 is then integrated by an integration circuit 24. A comparison circuit 26 compares the output 28 of the integrator, for each pulse, to a preset threshold value. When the output of the integration crosses the threshold value, the apparatus is then armed and an event detector 30, here shown as a zero crossing detector, detects the next event (here a zero crossing) in the input received signal over a line 31. Rectification may be either full wave or half wave; however, according to the preferred embodiment of the invention, half wave rectification is preferred. The particular arming method and apparatus employed herein is particularly reliable and is substantially insensitive to noise and jitter as described hereinafter.

Figure 2:
FIG. 2 is a display of transmitted, received, and rectified signals useful, in explaining the invention.
Figure 2:
Figure 2:

According to the integrated threshold arming method and apparatus, and referring to FIG. 2, line (c), the result of rectifying the received signal is a plurality of half-cycle sine waves (approximately) at first increasing in amplitude and then decreasing in amplitude. According to the preferred embodiment, it is the cumulative sum of the areas under, for example, each (positive) half cycle of the received signal which is employed to mark (the arming condition) a zero crossing (or other event) which, in turn, is used to determine the actual arrival time of the energy pulse.

The integral, I, of an individual half cycle of a sine wave of amplitude A is:

$$I = \int_0^\pi A \sin t \, dt = 2A$$

In other words, the area under each half cycle of a sine wave is simply proportional to the pulse amplitude of the half cycle. With respect to the received and rectified pulse, line (c) of FIG. 2, to the extent that each half cycle or segment is sinusoidal, the area under that segment is proportional to its amplitude. If, then, a sinusoidal signal increases linearly in ten cycles to a maximum amplitude, the relative area contributions of the positive half cycles, starting with the first half cycle, are given approximately by the arithmetic progression 0.2, 0.4, 0.6, . . . , 2.0. If one integrates these contributions, the sum increases as more and more half cycles are added. The results of the first ten half cycles, assuming a linearly increasing amplitude, are shown below:

| Number of half cycles | 1 | 2 | 3 | 4 | 5 | 6 | 7 | 8 | 9 | 10 |
|---|---|---|---|---|---|---|---|---|---|---|
| Relative Amplitude | .1 | .2 | .3 | .4 | .5 | .6 | .7 | .8 | .9 | 1.0 |
| Cumulative Sum | .2 | .6 | 1.2 | 2.0 | 3.0 | 4.2 | 5.6 | 7.2 | 9.0 | 11 |

The contributions and sums would be slightly different for an exponential amplitude or for a different "Q", but the ten cycle linear ramp envelope described above explains the significant advantages of the integrated threshold arming approach.

If the threshold of a comparator 26 (FIG. 3), responsive to the output of the integrator circuitry 24, is set in this example at 2.5, (midway between the sums for the fourth and fifth half cycles), a false arming will occur only if the amplitudes of all of the first four half cycles increase by twenty-five percent, or if the amplitudes of the first five half cycles all decrease by 16.67 percent. By comparison, considering the progression of half cycle amplitudes, if an amplitude based arming threshold is set to, say 0.45, a false arming will occur if the first four half cycles increase by 12 percent (0.4 to 0.45) or if the first five half cycles decrease by 10 percent (0.5 to 0.45). In this example, the integrated threshold is about twice as tolerant to amplitude fluctuations as the conventional arming based on amplitude alone. Similarly, if it were determined to arm earlier in the pulse, for example when the integral equals 0.8, (to arm on half cycle No. 3), then a false arming will occur if the first two half cycles increase by 34 percent or if the first three half cycles decrease by 34 percent. With amplitude based arming, at a threshold set to 0.25, false arming occurs if all of the half cycles increase or decrease by 20 percent. Again, the integrated threshold arming method is more reliable, that is, more tolerant to amplitude changes (and half-wave rectification is more tolerant to amplitude changes than is full-wave rectification). The integrated threshold thus provides a smoothing effect which translates to improved immunity to attenuation effects which may affect all of the cycles equally. The "smoothing" also provides better immunity to effects whereby only some of the cycles are distorted and to noise spikes which may have a high amplitude but are too brief in time duration to materially affect the integral value. Importantly, high frequency noise and signals which randomly add to some half cycles but subtract from others, tend to be disregarded to the extent that the integration cancels their bipolar contributions.

Figure 4:
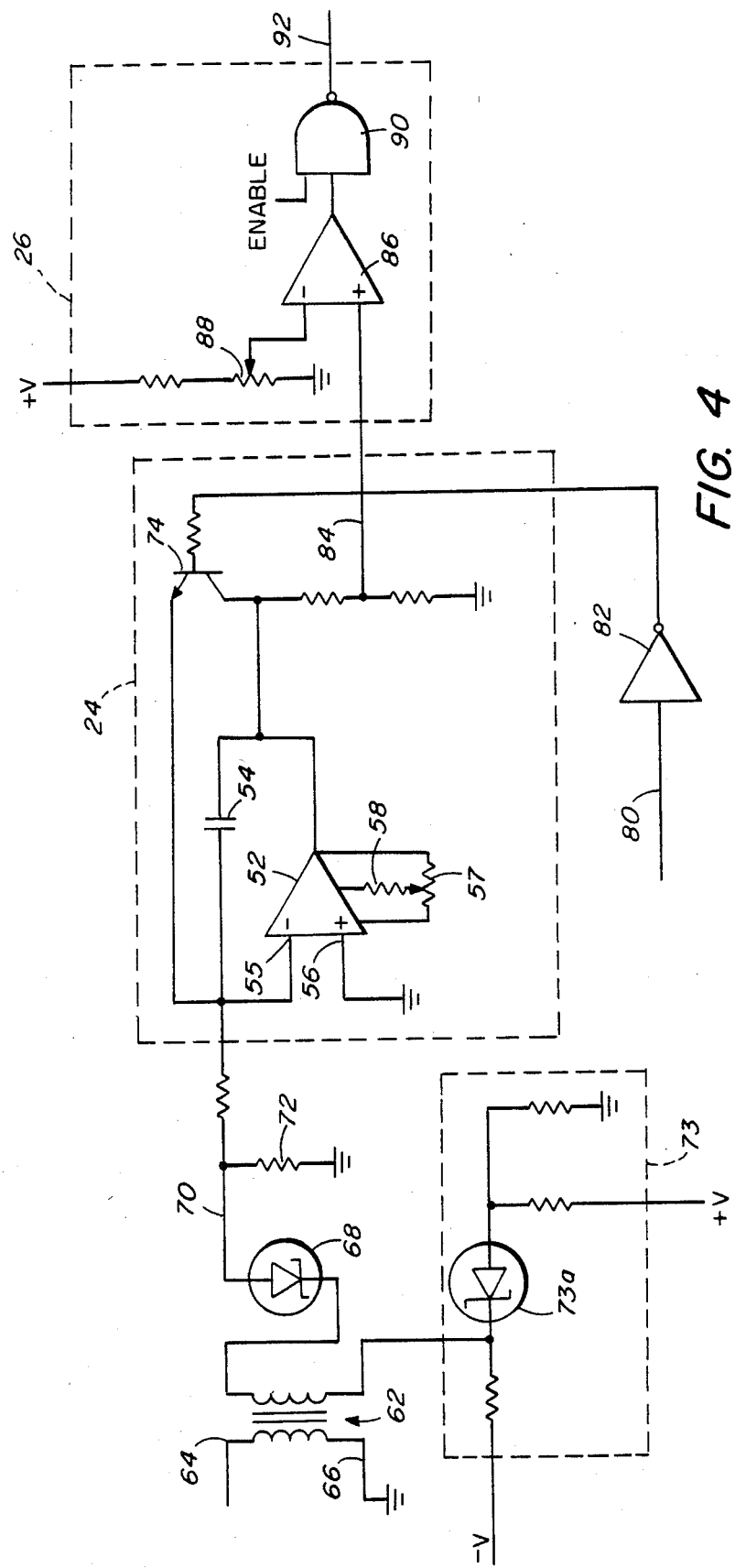
FIGS. 4 and 5 are more detailed electrical schematic diagrams describing a particularly advantageous implementation of the electrical circuitry according to the invention.

Referring now to FIG. 4, in a particularly preferred embodiment of the invention, the integration circuit 24 employs an operational amplifier 52 connected with a capacitor 54 in its feedback circuit connection to a negative amplifier input 55. The positive input 56 to amplifier 52 is grounded. An offset adjustment employing a potentiometer 57 and a series resistor 58 provides "zeroing" for the amplifier 52.

The input signal to the negative terminal input 55 of operational amplifier 52 is available from the rectification circuit 20. Circuit 20 has a transformer 62 which receives its input across input terminals 64, 66 (terminal 66 being grounded) and provides a rectified output (half wave rectification), from a rectifier 68, over a line 70. A resistor 72 provides a load for a bias network 73 when the amplifier 52 is not in its linear region of operation. Bias network 73 has a rectifying diode 73a which provides temperature compensation for diode 68. Both diodes 68 and 73a are Schottky diodes.

In accordance with the invention, integrator 24 integrates the half cycles of a received pulse signal. To reduce noise problems and to "zero" the output of the integrator at the beginning of a received pulse, the integrator is in a "reset" state until just prior to the expected receipt of the input signal pulse. The reset function is enabled using a transistor 74 having its emitter and collector connected across the capacitor 54. At turn on (i.e. reset), the output of the integrator "ramps down" to about −0.1 volts. This takes approximately 0.1 to 0.2 milliseconds, the time being set by potentiometer 57. The state of transistor 74 is controlled by the signal on its base which, at transistor turn-off, corresponds to a receive window during which a pulse of energy is expected to be available. At transistor 74 turn-off, the integrator 24 integrates the rectified signal on line 70.

Noise immunity is further enhanced by imposition of a deadband, that is, a voltage threshold below which the input signal is not integrated. In the illustrated embodiment, the deadband is provided by the turn-on voltage required for diode 68, typically about 0.4–0.5 volts for a Schottky diode. This voltage is effectively reduced further by bias network 73.

A receive gating signal is available over a line 80. The gating signal is inverted by an inverter 82 and is provided thereby to the transistor 74. The output of the integrator 24 available from a resistor divider, over a line 84, connects to the comparator 26. Comparator 26 employs a comparator integrated circuit 86, having one input connected to the integrator output over line 84 and its other input connected to the output of a potentiometer 88. Potentiometer 88 is connected between a reference voltage and ground. The comparator output is the arming signal and passes through a gating structure 90 and appears over a line 92. This signal changes state when the integrated signal from integrator circuitry 24 crosses the threshold value determined by potentiometer 88.

Figure 5:
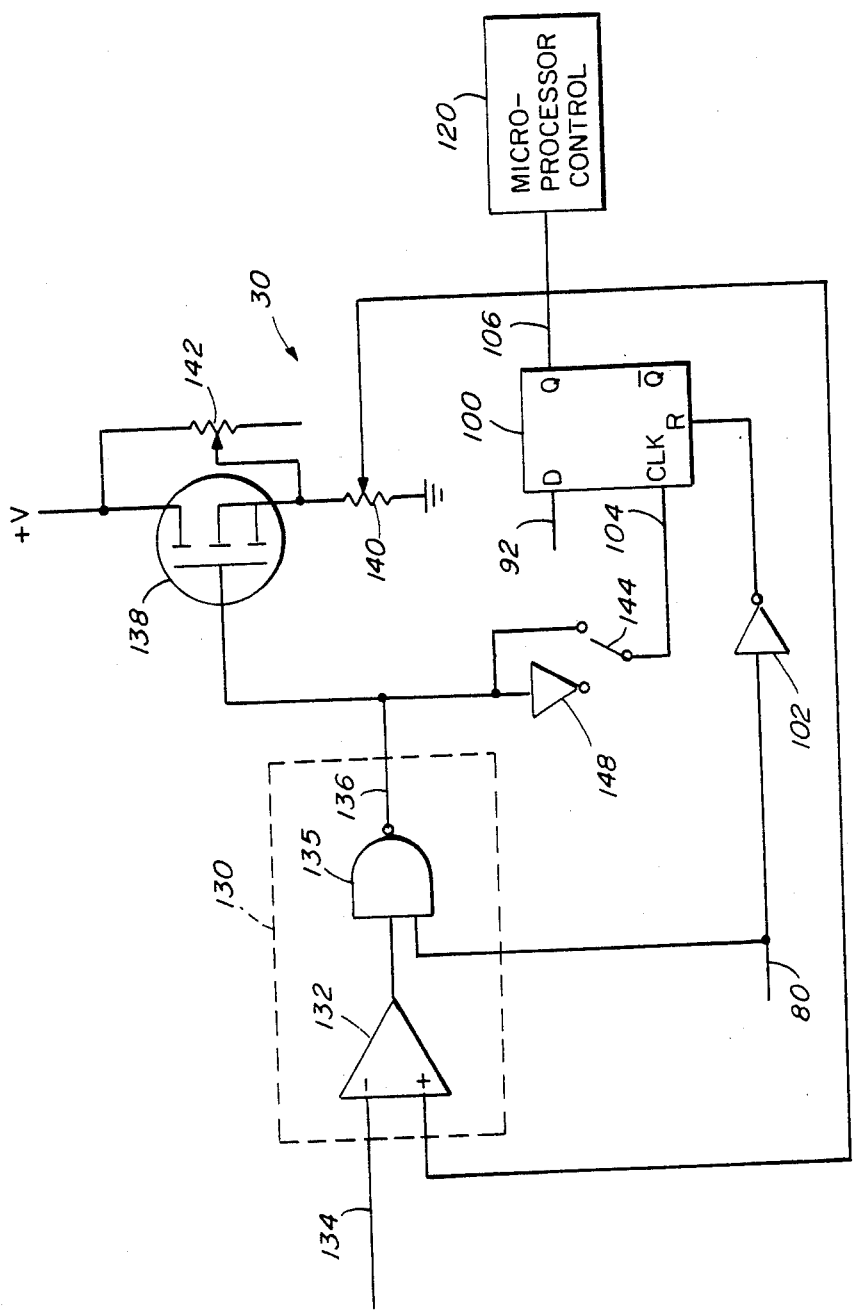

Referring to FIG. 5, the output of the integrated threshold circuitry over line 92, the arming signal, indicates an arming condition when the integrated value crosses the threshold value thereby changing the state of the output signal. This "change of state" enables an event recognition circuit, here the zero-crossing detector 30. Detector 30 employs a flip-flop 100 which, when initially enabled, is in the reset state. Flip-flop 100 has been previously reset by the gating window signal over line 80 (through an inverter 102). When clocked by a signal over a line 104, the flip-flop 100 indicates a zero crossing in the transducer generated receive signal, and that zero crossing signal output of flip-flop 100 over a line 106, is provided to further circuitry including a microprocessor controller 120 to set the time of arrival of the received pulse.

The zero crossing detector 30 further employs a gated comparator 130 having a comparator integrated circuit 132, one side of which receives the electrical pulse receive signal from the transducer over a line 134. A gate 135 is enabled by the gating signal over line 80. The pulse signal over line 134 has been passed through an automatic gain control (AGC) circuitry to provide a substantially constant input signal amplitude level even though changes in the physical media being monitored may occur.

The zero crossing detector employs a varying threshold level to improve zero crossing detection precision. In operation, with no signal present, the output of the zero crossing comparator 130, over a line 136, maintains a MOSFET 138 in an "on" condition. The threshold level is thereby set by an arming level potentiometer 140. In the illustrated embodiment, this quiescent level is a non-zero positive voltage. Thereafter, when a signal pulse is received, comparator 130 changes the state of its output signal when the quiescent threshold is exceeded. This causes the MOSFET 138 to turn off, thereby placing a variable resistor 142 in series with potentiometer 140. The threshold level is thereby effectively lowered, variable resistor 142 having a resistance substantially greater than the resistance of potentiometer 140. Thus, as the input signal approaches zero, going from a positive to a negative voltage (for the position of a switch 144 illustrated in the drawing), the lower threshold crossing is marked by the change of state of the signal on line 136. It is this change of state which acts to clock the flip-flop 100 thereby marking, by a signal over line 106, the first negative going zero crossing occurring after the arming signal over line 92 is received.

In this manner, the integrated threshold arming technique accurately, reliably, and repeatedly arms the event recognition detector at the same cycle of each received signal pulse over line 18. (In its other position, the switch 144 places an inverter 148 in series with the output of comparator 130 thereby causing detection of a negative to positive voltage at the threshold set by potentiometer 140.)

While the invention has been described with reference to a zero-crossing detector, it will be understood that the actual point to which time is measured at or after arming, can be any of a variety of signal threshold levels. For example, the level at which the arrival time is said to occur can be at any convenient absolute signal level, a selected fraction of the peak signal level, or even at a value greater than a particular cycle's maximum value, for example, at a level fifty per cent greater than the peak value of the first cycle following arming. This last alternative can be selected for measuring time at a point where the signal-to-noise ratio is large enough to permit a particularly high accuracy to be obtained.

The reliability of the integrated threshold arming circuit can be further improved by using the following further aspects of the invention.

Automatic Gain Control

Figure 6:
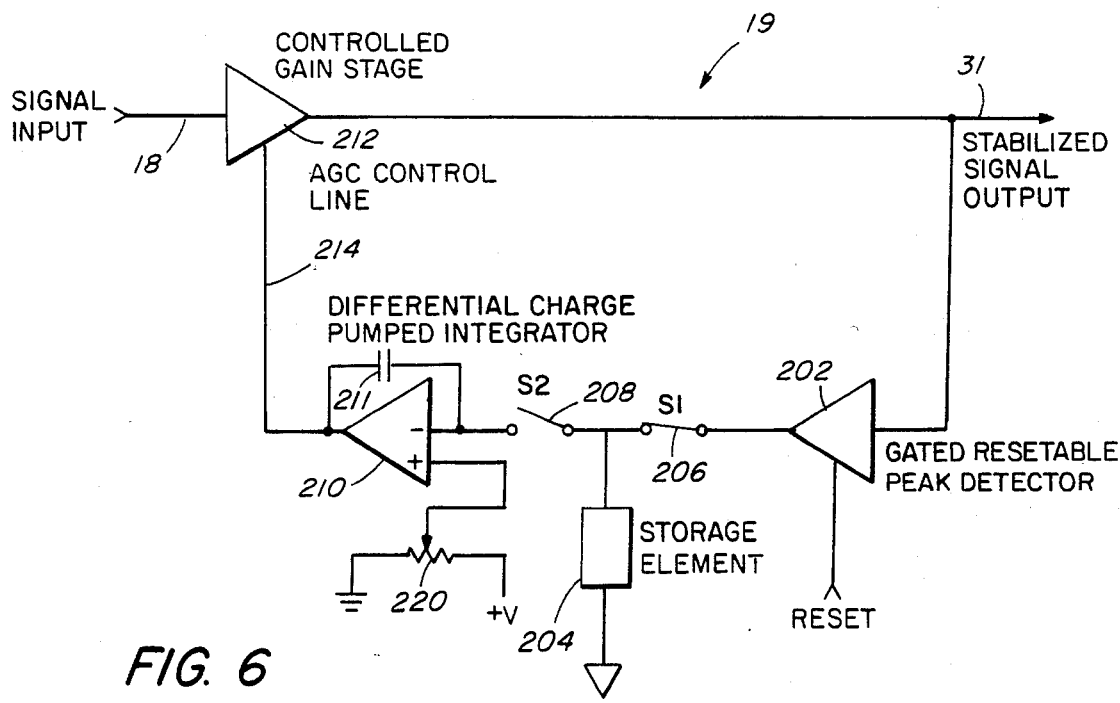
FIG. 6 is an electrical diagram of an automatic gain control circuit according to the invention.

According to the illustrated embodiment, the automatic gain control circuitry 19 is capable of tracking the envelope of both rapidly increasing and rapidly decreasing signals. Preferably circuitry 19 is equally responsive to increasing and decreasing amplitudes. Referring to FIG. 6, illustrated circuitry 19 has a gated, resettable peak detector 202, a storage element 204, the storage element typically being a capacitor, switches 206 and 208, which may be electrical or electromechanical, a differential "charged pumped" integrator 210 having an integrating capacitor 211 in its feedback loop, and a controlled gain amplifier 212, the gain being controlled by the automatic gain control signal level over a line 214. The input to the gain controlled amplifier is the "raw" input signal from, for example, the transducer 14 receiving the ultrasonic pulse energy in the fluid. The output of the transducer is provided to the gain control circuit 19 over line 18. The output of the gain controlled amplifier, over a line 31, is thus a stabilized signal output which is delivered, *inter alia*, to the rectification circuitry 20 and the zero crossing detector 30. That stabilized signal output is also provided to the gated resettable peak detector 202 wherein the automatic gain control amplifier operates in a feedback loop configuration.

Figure 7:
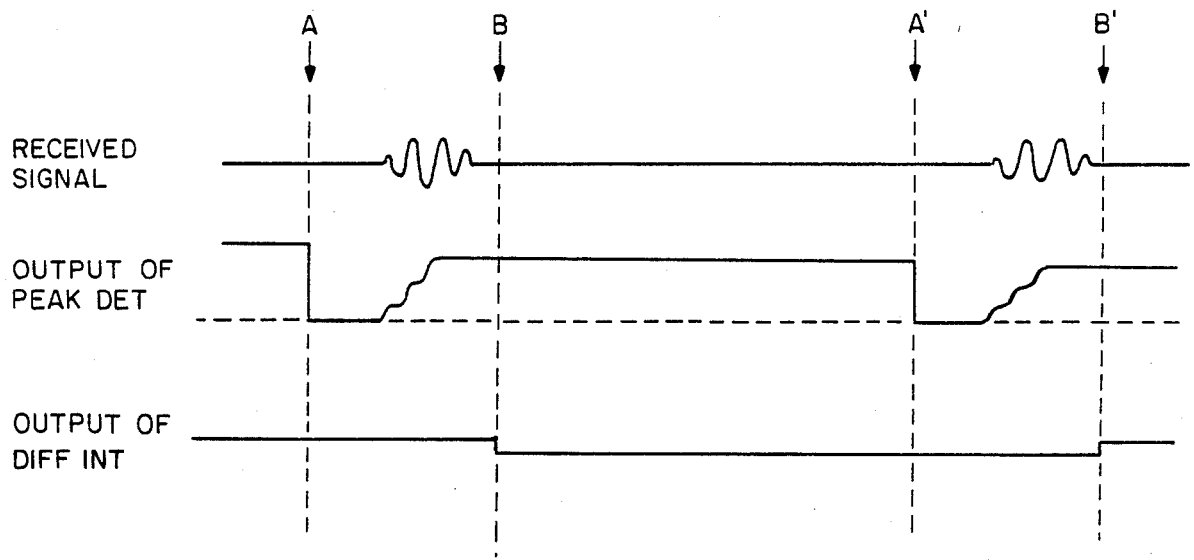
FIG. 7 is an illustration of the operation of the automatic gain control circuit of FIG. 6.

In operation, referring to FIGS. 6 and 7, at the beginning of a pulse, at time "A", the peak detector 202 has been reset to zero. The peak detector can be reset to zero using for example the receiver window pulse over line 80 (FIGS. 4 and 5). Upon receipt of the desired signal, the peak detector charges the storage element 204 to a voltage corresponding to the peak of the received signal. During this time switch 206 has been closed and switch 208 has been open. After the pulse of energy has been received, switch 206 is opened and switch 208 is thereafter closed. This occurs at a time "B" after receipt of the energy pulse but before receipt of the next signal energy pulse.

When switch 208 is closed, some of the charge stored in the storage element 204 is "dumped" into the differential integrator 210. The quantity of charge injected into the integrator 210 is proportional to the difference between the signal amplitude control voltage determined by a potentiometer 220 and the actual received peak signal amplitude. The "dumped" charge causes the output of the integrator 210, which is the automatic gain control signal voltage, to apply a correcting voltage to control the gain of amplifier 212. The peak detector is thereafter reset by the gating signal over line 80, switches 206 and 208 reversing their condition, so that the storage element is discharged and the cycle repeats again for the next received pulse.

Figure 8:
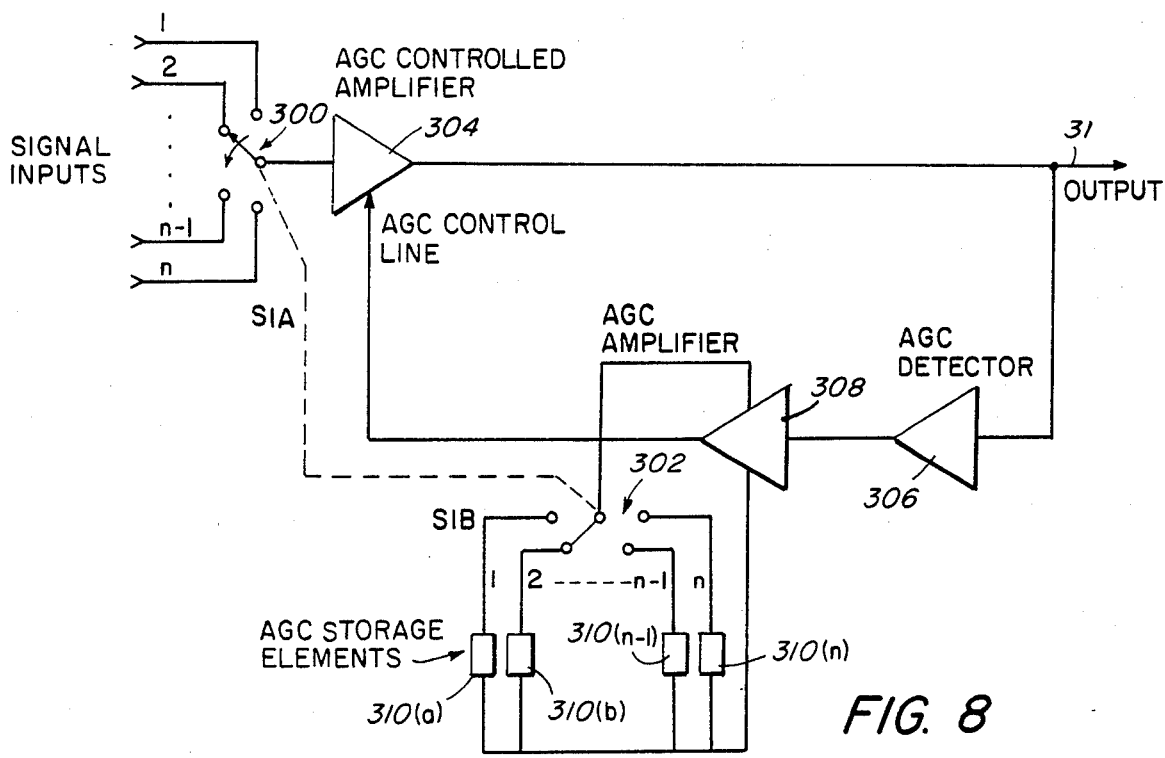
FIG. 8 is a schematic block diagram of a multipath automatic gain control circuit according to the invention.

Referring now to FIG. 8, according to the invention, a single automatic gain controlled amplifier receiver circuitry can be employed in connection with multiple measurement paths by employing a synchoronized switching arrangement along with storage elements in association with each path. In accordance with this aspect of the invention, the circuitry includes multiposition switches 300, 302, which synchronously connect automatic gain controlled amplifier 304 and an automatic gain control peak detector 306, which operates in connection with an amplifier 308, to different paths (1, 2, ..., n-1, n) and different storage elements 310a, 310b, ..., 310n-1, 310n. Thus, according to the invention, each storage element is employed to hold accurate automatic gain control level data for an associated transmission path. By using a previously stored automatic gain control level for each path, the automatic gain control circuitry is capable of providing correct compensation for each path immediately upon selection of that path.

Thus, switches 300 and 302 operate synchronously, at speeds up to and exceeding fifty positions per second, and movement of switch 300 to a path "m", is automatically accompanied by the movement of switch 302 to connect storage element 310(m) to the circuit. The storage elements can also be updated each time a path is selected thereby allowing the automatic gain control loop to compensate for changes in the path signal strength.

Figure 9:
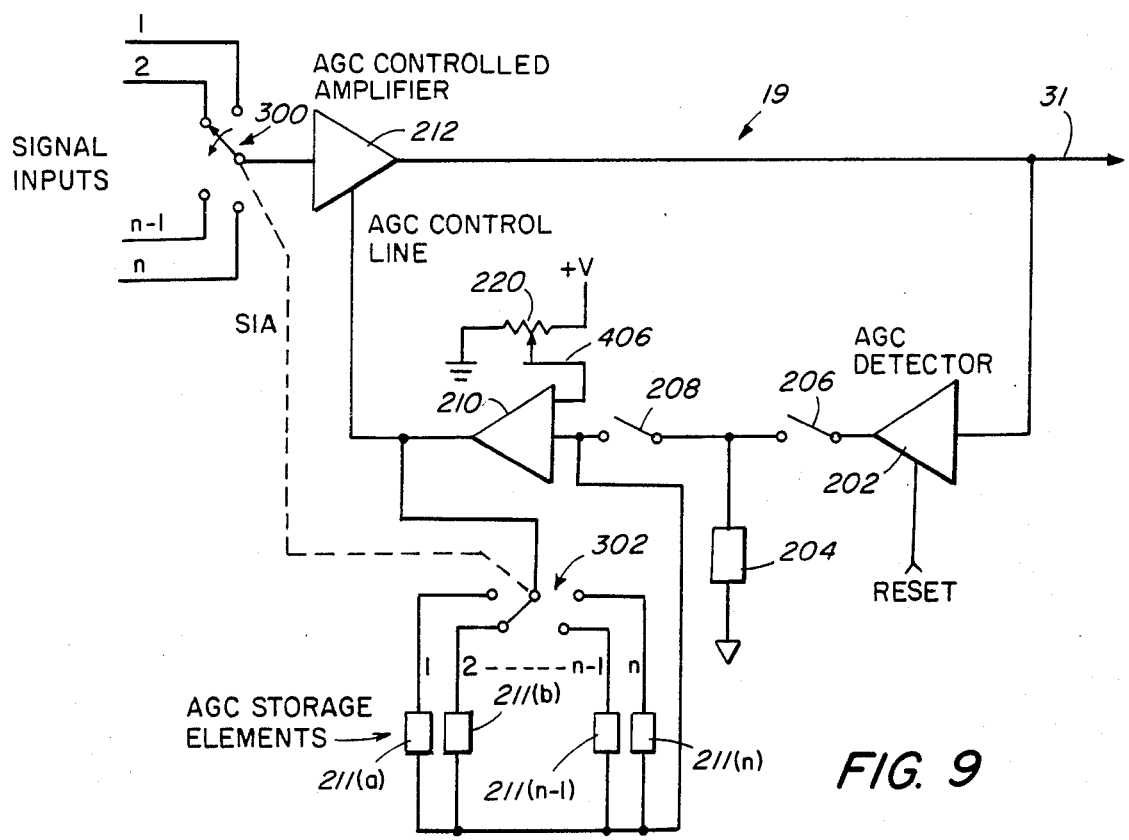
FIG. 9 is an electric block diagram showing the automatic gain control amplifier of FIG. 6 in a multipath environment.

In addition, wherein multiple paths are measured using a single automatic gain control receiver, the automatic gain control circuitry described in connection with FIG. 6 is preferably employed. The FIG. 6 circuitry can be modified to allow use of multiple storage elements such as those shown in FIG. 8. The resulting AGC circuitry, illustrated in FIG. 9, operates in a manner identical to that described in connection with FIG. 6 except that synchronous switches 300, 302 are employed for providing the necessary switching circuitry to synchronously hold and store the AGC control signals in capacitors $211(a)$, $211(b)$, ..., $211(n)$, and connect amplifier 212 to the correct input line.

Slipped Cycle Improvement

As noted above, the arrival time of a narrow band signal is typically measured by picking a particular zero crossing, for example, the fifth, as the nominal arrival point of the signal. A zero crossing is relatively easy to detect however the nature of a narrow band signal, that is a plurality of cycles each having closely related amplitude characteristics, makes it difficult as noted above to consistently pick out the same zero crossing under varying signal conditions. For this reason therefore the integrated threshold arming method and apparatus described hereinabove is employed. In addition to using the integrated threshold arming method and apparatus however, further reliability can be achieved by using, if available, the a priori knowledge that the difference in arrival times of two successive pulse signals, one upstream and one downstream, will not vary more than a predetermined calculable amount, for example, less than one period of the interrogation pulse. As a result, if the desired information is not the absolute arrival time of the signal but rather the difference in arrival time between two pulse signals (which information can be sufficient to measure volumetric fluid flow if the sound velocity in the fluid is known), then a "slipped cycle" correction method and apparatus can be employed to augment the measurement of the same zero crossing for each received pulse. In fact, if the only information needed is the relative difference in arrival times between two signals, then the "slipped cycle" correction method and apparatus can be employed by itself.

The "slipped cycle" method uses the knowledge, if accurate for the circumstances, that the difference in upstream and downstream arrival times for a unidirectional flow will, with certain constraints imposed upon flow rate of change, always be less than one cycle of the received signal. If on the other hand the difference is expected to be greater than one cycle of the received signal, this method cannot be employed. (One solution, here, is to use a lower interrogation frequency to reduce the "slip" to one cycle.)

Figure 10:
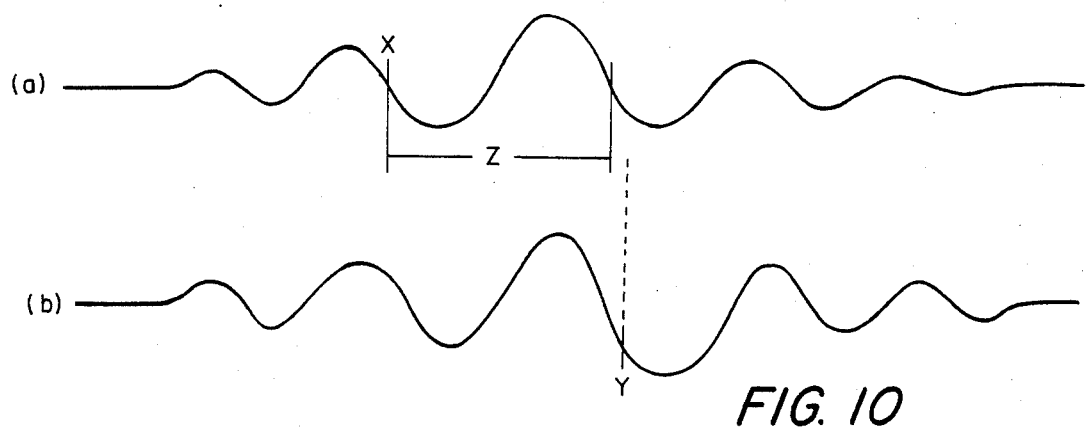
FIG. 10 is an illustration useful in explaining the slipped cycle method of operation.

The "slipped cycle" method employs the step of taking the raw arrival time, which may have been measured initially to an incorrect zero crossing, and adding or subtracting multiples of the received signal period to the time difference to make that time difference no greater than one period in time duration. For example, referring to FIG. 10, at line (a) there is a first received narrow bandwidth pulse with the detected zero crossing marked as "X". In line (b), there is a second received pulse with a detected zero crossing at "Y". The time distance $T1 = Y - X$ is greater than one period "Z" of the received signal. If it is known a priori that the difference in time duration between the two signals should be less than one period, then an amount of time equal to one period can be added or subtracted to the difference until the difference is a positive number, $dt = Y - X + NP$, where P is the period of the received signal, N is a positive or negative integer, and dt, the adjusted difference in transit times, is less than the period of the received signal. In the example of FIG. 10 therefore, a single period is subtracted from the difference and thereby, $Y - X - P$ is chosen as the corrected time difference.

Since the time difference for bipolar flow can be either positive or negative, then there is, for bidirectional flow, an additional restriction on the maximum value of dt. Thus, for bipolar flow, dt cannot exceed plus or minus one-half of the received signal period. However, if the flow is bidirectional, but the direction of flow is known, then dt generally can have a maximum value in excess of one-half of the received signal period but still less than one full period. For example, if breathing is being measured and if the intervalometer is instructed that the subject is inhaling (or exhaling) then the ambiguity caused by unknown flow direction can be avoided.

The "slipped cycle" method can be further extended to the application where the flow is known to lie within a predetermined range, for example between velocities V1 and V2. As long as the time difference in this range is less than one period, the slipped cycle method can be implemented. For example, assume a signal period of ten microseconds. Then, assume at a flow V1, the transit time equals 21 microseconds and at a flow V2, the expected transit time equals 29 microseconds. The difference in transit time, 8 microseconds, is less than the assumed signal period and even though the individual transit times exceed the signal period, the slipped cycle method is still applicable.

The slipped cycle correction method can most advantageously be implemented by using microprocessor controller 120 which allows for the correction to be accomplished after the zero-crossing data has been transferred into the microprocessor's memory. In order for the microprocessor controller to accurately provide the necessary information however, the exact signal period must be provided. Using an analog transmitter, the period can be entered into the microprocessor using manually controlled switches after the transmitter has been tuned to an optimum frequency. However, to avoid the inconvenience of setting the period on the switches and the inaccuracies which are associated with determining the exact period of the received signal (within say one percent), the transmission frequency can be digitally derived from a quartz clock controlled oscillator 399. The quartz oscillator provides a highly stable known frequency thereby allowing the microprocessor to be preprogrammed with the signal period and thus eliminating the need for both entering the data manually by the switches, and for expending additional effort and time to measure the signal period.

The slipped cycle correction procedure is further extendable to correcting the arrival time of a single received pulse signal. The sole criterior is whether an "expected" arrival time, that is, when the pulse should be received, is known a priori within a range of one cycle. If that a priori knowledge is available, the measured time of arrival can be adjusted, as noted above, to be within one-half of a cycle time of the "expected" arrival time. The adjustment is effected by adding or subtracting multiples of the cycle period to the measured arrival time. Thus, if the measured arrival time is "MT" and the "expected" arrival time is "ET", then the measured time is adjusted so that $$|MT-ET-NP| < (\tfrac{1}{2})P$$

where, as noted above, N is a positive or negative integer and P is the cycle period.

Parameter Discrimination

According to the invention, the microprocessor controller can also provide a further error rejection capability by responding to an amplitude discriminator circuit 400 for ignoring data from received pulses wherein the received amplitude is outside predetermined prescribed ranges. The amplitude discrimination circuit makes a comparison between the amplitude of each received signal and a reference amplitude. If the magnitude of the difference between the received signal amplitude and the reference amplitude is greater than a predetermined value, then an error signal is provided to the microprocessor controller over a line 402 indicating that the received signal is out of tolerance. The microprocessor controller responds to this amplitude error information, and to the arrival time of the received signal, for determining if the transit information derived from the received signal is likely to be good or bad. If the probability is high that the transit information is bad, due to such factors as electrical or acoustical noise or flow turbulence, the transit information from the signal can be rejected and thereby not used by the microprocessor in further calculations. For example, if the received signal amplitude is greater than 10 percent above the reference amplitude, OR if the signal amplitude is more than 10 percent below the reference amplitude, OR if the transit time is greater than a predetermined maximum value, OR if the transit time is less than a predetermined minimum value, OR if the difference between the transit times along two paths is greater than a predetermined maximum, then the data derived from the received signal is considered in error and is not employed in further calculations.

Other criteria, including for example the rate of change of transit time or amplitude information, can also be employed in determining an error in the input signal and therefore results in a powerful method for discrimination between good and bad received data.

Figure 11:
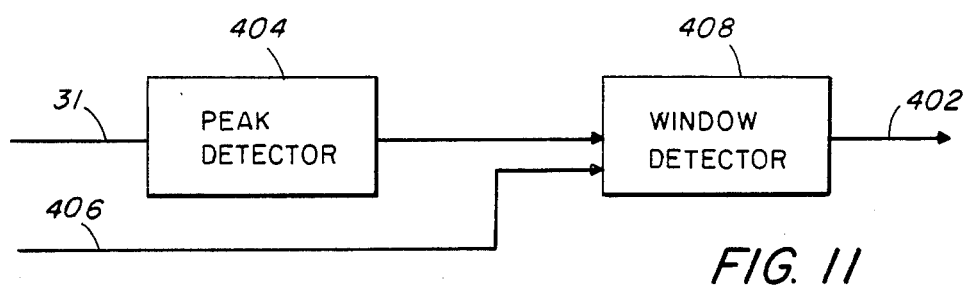
FIG. 11 is an electrical block diagram of an amplitude discrimination circuit according to the invention.

Referring to FIG. 11, an amplitude discrimination circuit 400 employs a peak detector 404 to determine signal amplitude. The received signal is peak detected after being amplified by the automatic gain controlled amplifier 19. The automatic gain control reference set point over a line 406 (FIG. 9) then provides a convenient level with which to compare the received signal amplitude.

A window detector 408, with its upper and lower "trip points" set slightly higher and lower respectively than a level derived from the automatic gain reference set point, is employed for determining if the peak amplitude of the received signal is within acceptable limits. The output of the window detector connects to the microprocessor allowing the received signal amplitude to be used in combination with other information transmitted to the microprocessor for determining if a received signal represents good or bad data.

Figure 12:
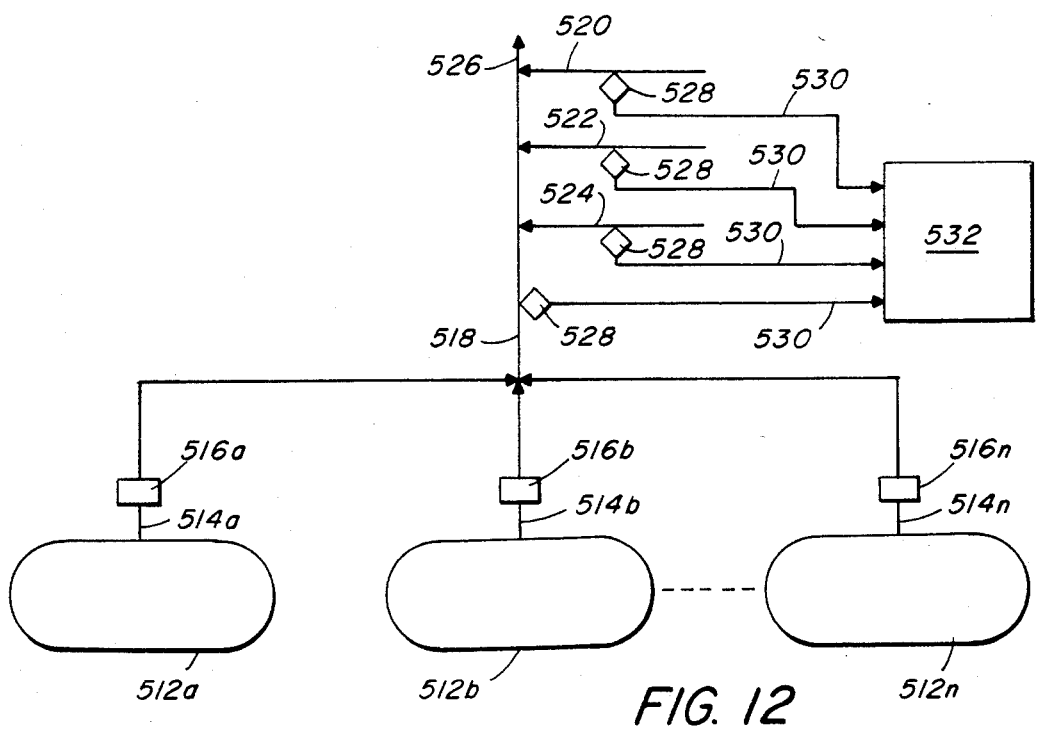
FIG. 12 is a schematic representation of a typical petrochemical application in which the invention is particularly advantageous.

Referring to FIG. 12, in a particular application, the invention can be employed in connection with an intervalometer useful in a petrochemical manufacturing facility. The facility has a plurality of process stations 512a, 512b, . . . , 512n, wherein different manufacturing processes or process stages can be performed. Typically these manufacturing stages are interconnected to form a complete manufacturing process by piping and control connections (not shown). Each of the process stages further includes a single discharge conduit 514a, 514b, . . . , 514n, each having associated therewith a safety valve 516a, 516b, . . . , 516n respectively. The discharges from the stages are collected in a single header 518 which typically has between ten and twenty safety valves and related conduits connected thereto. Further, headers 520, 522, and 524 from other manufacturing stations can be collected into increasingly larger headers until all of the discharges from an entire manufacturing process can be collected into a single large header 526 (the flare stack). The gases from header 526 can be ignited and burned in an elevated flare or burner pit and from there can be safely vented to the environment.

In accordance with this particular application of the invention, the intervalometer is employed to aid in determining the gas flow rate through the headers. Thus, each header can have secured thereto a flow measurement transducer apparatus 528 incorporating, for example, the upstream and downstream transducers. The intervalometer electronics 532 are connected through cables 530 to the transducer elements. The electronics thus include that circuitry illustrated in FIG. 2 which occurs after the transducer 14.

In accordance with this application, one or more of the safety valves 516a, 516b, . . . , 516n can leak and generally the leakage rate is small and of no great concern. At other times, however, the valves can leak excessively for one of many reasons, resulting in a substantial flow through the various headers. The quantity of flow through the headers as well as its content can be important parameters in determining the efficiency of the manufacturing process as well as the safety and efficiency of the flare stack system. The intervalometer herein can be employed for each header or for the flare stack itself to determine the quantity of flow passing therethrough.

Additions, subtractions, deletions, and other modifications of the described preferred embodiments will be obvious to those practiced in the art and are within the scope of the following claims.

What is claimed is:

1. An intervalometer for determining the transit time of ultrasonic energy traversing a fluid medium, said intervalometer comprising
 a transmitting transducer for emitting a pulse of ultrasonic energy, a receiving transducer for receiving said ultrasonic energy and for generating ancelectrical signal in response thereto, an automatic gain controlled amplifier circuit for amplitude stabilizing said electrical signal, said amplifier circuit having means for tracking both a rapidly increasing and a rapidly decreasing signal amplitude of the electrical signal representing a said energy pulse, and a transit time measurement means responsive to said stabilized electrical signal for determining said transit time.

2. The intervalometer of claim 1 further wherein said gain controlled circuit comprises a gated, resettable amplitude detector connected to receive said stabilized signal, a storage element switchably connected to said amplitude detector for storing a signal representative of said stabilized signal amplitude, a differential integrator having a control signal output, said integrator being switchably connected to said storage element and being further connected to a signal reference level, a controlled gain amplifier connected to and controlled by said control signal output of said integrator, means for connecting said detected to said storage element during receipt of an energy signal and for connecting said integrator to said storage element for a time duration following receipt of said energy signal, said storage element being connected to one only of said detector and integrator at a time, and means for resetting said amplitude detector prior to the receipt of a next energy signal.

3. The intervalometer of claim 2 wherein said transmitting transducer emits a pulse of ultrasonic energy, said storage device comprises a capacitor, said detector comprises a peak detector circuit, and said integrator includes means for responding to the difference between the reference voltage level and a charge input from the capacitor.

4. the intervalometer of claim 1 further wherein said automatic gain control amplifier is equally responsive to increasing and decreasing amplitudes.

5. An intervalometer for determining the transit time of ultrasonic energy traversing a fluid medium along a plurality of paths, said intervalometer comprising a plurality of transmitting transducers, each transmitting transducer for emitting a pulse of ultrasonic energy, a plurality of receiving transducers, each receiving transducer associated with a transmitting transducer for receiving ultrasonic energy transmitted therefrom for generating an electrical output signal in response thereto, an automatic gain controlled amplifier circuit for providing an amplitude stabilized output signal in response to an electrical signal input thereto and according to a control signal input thereto, a plurality of controlling storage elements, each storage element, when connected to said gain controlled amplifier, providing said control signal input thereto, synchronous switching means for synchronously switching a first and a second switch means, each switch means connecting a selected one of a plurality of switch input lines to a switch output line, and said switching means connecting a selected one of said receiving transducer output signals to said gain controlled amplifier and for synchronously connecting a selected one of said controlling storage elements to said gain controlled amplifier, whereby a single gain controlled amplifier can be rapidly cycled among said receiving transducers.

6. The intervalometer of claim 5 wherein each said storage element comprises a capacitor, and said gain controlled amplifier when connected to a storage element, updates the stored value in the storage element in accordance with a said connected transducer output signal.

7. The intervalometer of claim 6 further comprising means for switching said switching means at a rate greater than 50 positions per second.

8. In an intervalometer for measuring the transit time difference between the time duration required for an ultrasonic energy pulse to traverse a fluid first in an upstream direction and then in a downstream direction, the measurement method comprising the steps of measuring an upstream transit time based upon an event recognition in an upstream received energy pulse, measuring a downstream transit time based upon said event recognition in a downstream received energy pulse, each said energy pulse having a plurality of repeating cycles, said event being a characteristic of one of said cycles, and said cycles being characterized by a repetitive period, and generating a measurement of said time difference by differencing said upstream and downstream transit times, and adjusting said transit time difference by multiples of said repetition period time until said difference is within a predetermined time range.

9. The method of claim 8 further comprising the step of employing said adjusted time difference for determining the volumetric flow of a fluid through a pipeline.

10. The method of claim 9 further wherein said flow is a unidirectional flow, and said adjusted transit time difference is less than the time of one period.

11. The method of claim 9 further wherein said flow is a bidirectional flow, and said adjusted transit time difference has a magnitude less than the time of one-half of a period.

12. The measurement method of claim 11 further comprising the steps of determining said fluid flow direction, and using said direction to determine said maximum 13. The measurement method of claim 8 wherein said event recognition detects a zero crossing of said upstream and downstream received energy pulses.

14. The measurement method of claim 8 further comprising the step of generating said transmitted energy pulse using a digital circuit transmitting means.

15. In an intervalometer for determining the transit time of an ultrasonic energy pulse traversing a fluid medium, an intervalometer measuring method comprising the steps of transmitting an ultrasonic energy pulse from a first tranducer, receiving said transmitted ultrasonic energy pulse and generating an electrical signal in response thereto, measuring the transit time of said energy pulse based upon an event recognition in said received electrical signal, said energy pulse having a plurality of repeating cycles, said event recognition based upon a characteristic of one of said cycles, and said cycles being characterized by a repetition period, and adjusting the measured transit time of said energy pulse, when the difference between the measured transit time and an expected measured transit time has a magnitude greater than one-half of the cycle period, by changing the measured transit time by one or more periods of said cycle repetition so that the difference between the adjusted transit time and an expected value falls within a predetermined range.

16. In an intervalometer for determining the transit time of an ultrasonic energy pulse traversing a fluid medium, said intervalometer measuring method comprising the steps of transmitting an ultrasonic energy pulse from a first transducer, receiving said transmitted ultrasonic energy pulse and generating an electrical signal in response thereto, measuring the transit time of said energy pulse based upon an event recognition in said received electrical signal, said energy pulse havinga plurality of repeating cycles, said event recognition based upon a characteristic of one of said cycles, and said cycles being characterized by a repetition period, adjusting the measured transit time of said energy pulse by changing the measured transit time by one or more periods of said cycle repetition so that the difference between the adjusted transit time and an expected value falls within a predetermined range, and measuring said transit time by detecting a zero crossing of said electrical signal, and wherein said difference has a magnitude less than one-half of the cycle period.

17. An intervalometer for determining the transit time of an ultrasonic energy pulse traversing a fluid medium, said intervalometer comprising a transmitting transducer for emitting said ultrasonic energy, a receiving transducer for receiving said ultrasonic energy and for generating an electrical signal in response thereto, an automatic gain controlled amplifier circuit receiving said electrical signal and for outputing an amplitude stabilized electrical signal, means for determining amplitude limits of said stabilized electrical signal and for providing a bad signal indication when said amplitude of said stabilized signal is outside a predetermined allowable range of values, and a transit time measurement means responsive to said stabilized electrical signal for determining said transit time and responsive to said bad signal indication for determining whether said transit time represents bad data.

18. The intervalometer of claim 17 further wherein said transit time measurement means comprises means for determining whether a transit time difference is within an allowable narrow range of time durations, said narrow range being less than a period of the frequency of said emitted energy and for discarding said data should said transit time difference be outside said transit time difference range.

19. The intervalometer of claim 17 further wherein said determining means comprises a peak amplitude detection circuit.

20. Apparatus for determining the transit time of ultrasonic energy traversing a header in a flare stack system comprising a plurality of processing stations, each processing station having associated therewith a safety discharge conduit and a safety discharge valve connected for controlling discharge from said processing station to said conduit, at least one header conduit, each conduit connected to a plurality of said discharge conduits, a plurality of transmitting transducers mounted in association with said headers, each transmitting transducer adapted for emitting a pulse of ultrasonic energy, a plurality of receiving transducers mounted in association with said headers, each receiving transducer associated with a transmitting transducer for receiving ultrasonic energy transmitted therefrom and for generating an electrical output signal in response thereto, means for exciting said transmitting transducers for emitting ultrasonic energy therefrom, means for measuring an upstream transit time and a downstream transit time for the propagation of said energy between said transducers in an upstream and a downstream direction respectively, said measuring means including an automatic gain controlled amplifier circuit for providing an amplitude stabilized output signal in response to said electrical output signal input thereto and according to a control signal input thereto, a plurality of controlling storage elements, each storage element, when connected to said gain controlled amplifier, providing said control signal input thereto, synchronous switching means for synchronously switching a first and a second switch means, each switch means connecting a selected one of a plurality of switch input lines to a switch output line, and said switching means connecting a selected one of said receiving transducer output signals to said gain controlled amplifier and for synchronously connecting a selected one of said controlling storage elements to said gain controlled amplifier, whereby a single gain controlled amplifier can be rapidly cycled among said receiving transducers.

21. Intervalometer apparatus for determining the transit time of a bandwidth limited pulse of ultrasonic energy traversing a fluid medium comprising a transmitting transducer for emitting a pulse of ultrasonic energy, a receiving transducer for receiving said ultrasonic energy and for generating an electrical receive signal in response thereto, an automatic gain controlled amplifier circuit for amplitude stabilizing said electrical signal, said amplifier circuit having means for tracking both a rapidly increasing and a rapidly decreasing signal amplitude, arming means responsive to said stabilized signal for generating an arming electrical signal representative of an armed condition, said arming means comprising a signal integrator responsive to said receive signal for generating said arming signal when an integrated value, dependent upon said stabilized signal for a said energy pulse, crosses a threshold value, and event recognition means responsive to said arming signal for detecting an event occurring in said receive signal during said armed condition, said event determining the arrival time of said bandwidth limited pulse.

22. The intervalometer of claim 21 wherein there are a plurality of receiving transducers each generating a receive signal and further wherein said automatic gain controlled amplifier circuit comprises amplifier means responsive to a control signal input thereto, a plurality of controlling storage elements, each storage element, when connected to said amplifier means, providing said control signal input thereto, synchronous switching means for synchronously switching a first and a second switch means, each switch means connecting a selected one of a plurality of switch input lines to a switch output line, and said switching means connecting a selected one of said receiving transducer receive signals to said gain controlled amplifier and for synchronously connecting a selected one of said controlling storage elements to said amplifier means, whereby a single gain controlled amplifier can be rapidly cycled among said receiving transducers.

23. The intervalometer of claim 22 further comprising means for determining amplitude limits of said stabilized electrical signal and for providing a bad signal indication when said amplitude of said stabilized signal is outside a predetermined allowable range of values, and a transit time measurement means responsive to said event recognition means for determining said transit time and responsive to said bad signal indication for determining whether said transit time represents bad data.

24. A method for determining the transit time difference of upstream and downstream received, bandwidth limited pulses of ultrasonic energy traversing a fluid medium comprising the steps of transmitting an ultrasonic energy pulse from an upstream and a downstream transducer, receiving said transmitted ultrasonic energy pulses and generating an electrical receive signal in response to each received pulse, generating in response to each receive signal an arming electrical signal representative of an armed condition, said generating step comprising the step of integrating the receive signal for generating the arming signal when an integrated value, dependent upon the receive signal, crosses a threshold value, detecting, in response to each said arming signal, an event occurring in said receive signal during the armed condition, the event determining the arrival time of the bandwidth limited pulse, measuring an upstream transit time based upon said event recognition in an upstream received energy pulse, measuring a downstream transit time based upon said event recognition in a downstream received energy pulse, each said energy pulse having a plurality of repeating cycles, said event being a characteristic of one of said cycles, and said cycles being characterized by a repetition period, and generating a measurement of said time difference by differencing said upstream and downstream transit times, and adjusting said transit time difference by multiples of said repetition period time until said difference is within a predetermined time range.

25. The method of claim 24 further comprising the steps of determining amplitude limits of said received energy pulse and providing a bad signal indication when said amplitude of said received energy pulse is outside a predetermined allowable range of values, and responsive to said bad signal indication, determining whether said time difference represents bad data.

26. Intervalometer apparatus for determining the arrival time of a bandwidth limited energy pulse of ultrasonic energy comprising pulse receiving means responsive to said pulse for generating an electrical receive signal representing the undulations of the pulse, arming means responsive to said receive signal for generating an arming electrical signal representative of an armed condition, said arming means comprising a signal integrator responsive to said receive signal for generating said arming signal when an integrated value, dependent upon said receive signal for a said energy pulse, crosses a threashold value, said integrator further comprising an operational amplifier connected in an integrating configuration, and ramp down circuitry for forcing said integrator toward a predetermined constant voltage value in the absence of said receive signal, and event recognition means responsive to said arming signal for detecting an event occurring in said receive signal during said armed condition, said event determining the arrival time of said bandwidth limited pulse.

27. Intervalometer apparatus for determining the arrival time of a bandwidth limited energy pulse of ultrasonic energy comprising pulse receiving means responsive to said pulse for generating an electrical receive signal representing the undulations of the pulse, arming means responsive to said receive signal for generating an arming electrical signal representative of an armed condition, said arming means comprising a signal integrator responsive to said receive signal for generating said arming signal when an integrated value, dependent upon said receive signal for a said energy pulse, crosses a threshold value, said integrator further comprising a deadband threshold circuitry for blocking said receive signal prior to integration when said signal has a value within a predetermined range, event recognition means responsive to said arming signal for detecting an event occurring in said receive signal during said armed condition, said event determining the arrival time of said bandwidth limited pulse, and said deadband circuitry having a Schottky diode for rectifying said receive signal and for blocking said signal when said diode is in a turnoff state, and a biasing network adapted to operate with said diode for adjusting said predetermined range.

28. The intervalometer of claim 27 wherein said biasing network further has a second Schottky diode for providing temperature compensation to said integrator circuit.

* * * * *